(12) United States Patent
Bellmann et al.

(10) Patent No.: US 6,599,944 B1
(45) Date of Patent: Jul. 29, 2003

(54) OPHTALMIC COMPOUND WITH EXTENDED DWELL TIME ON THE EYE

(75) Inventors: Gunther Bellmann, Berlin (DE); Gudrun Claus-Herz, Berlin (DE)

(73) Assignee: Bausch & Lomb Incorporated, Rochester, NY (US)

( * ) Notice: Subject to any disclaimer, the term of this patent is extended or adjusted under 35 U.S.C. 154(b) by 0 days.

(21) Appl. No.: 09/171,344

(22) PCT Filed: Mar. 6, 1997

(86) PCT No.: PCT/EP97/01138

§ 371 (c)(1),
(2), (4) Date: May 19, 2000

(87) PCT Pub. No.: WO97/38674

PCT Pub. Date: Oct. 23, 1997

(30) Foreign Application Priority Data

Apr. 15, 1996 (DE) .......................................... 196 14 823

(51) Int. Cl.⁷ .......................... A61K 31/14; A61K 47/00
(52) U.S. Cl. .......................... 514/643; 514/781; 514/912
(58) Field of Search ................. 514/643, 781, 514/912

(56) References Cited

U.S. PATENT DOCUMENTS

| | | | | |
|---|---|---|---|---|
| 4,053,628 A | 10/1977 | Stevenson et al. | .......... | 424/283 |
| 4,271,143 A | 6/1981 | Schoenwald et al. | ....... | 252/106 |
| 4,738,851 A | 4/1988 | Schoenwald et al. | ....... | 424/488 |

FOREIGN PATENT DOCUMENTS

| | | | | |
|---|---|---|---|---|
| DE | 22 23 237 C2 | 1/1985 | .......... | A61K/31/35 |
| DE | 34 15663 A1 | 10/1985 | .......... | A61K/31/40 |
| DE | 27 14676 C2 | 3/1987 | .......... | A61K/31/765 |
| DE | 196 14 823 A1 | 10/1997 | .......... | A61K/31/14 |
| EP | 0 470 667 A1 | 8/1991 | .......... | A61K/31/495 |
| FR | 2 678 832 A | 7/1991 | ............ | A61K/9/09 |
| FR | 2 679 773 | 7/1991 | .......... | A61K/31/045 |
| JP | 01246227 | 10/1989 | .......... | A61K/47/40 |
| WO | WO 94/10976 | 5/1994 | ............ | A61K/9/00 |
| WO | WO 94/15597 | * 7/1994 | | |

OTHER PUBLICATIONS

Patent Abstracts of Japan "Prevention of Incompatibility of Compounding of Aqueous Preparation Containing Benzalkonium Chloride" Section No. 670, vol. 13, No. 589, P:10 (19891225).

CIP–Kurzitelaufnahme der Deutschen Bibliothek Fiedler, Herbert P. Lexikon der Hilfsstoffe fur Pharmazie, Kosmetik und angrenzende Gebiete / von Herbert P. Fiedler—2. uberarb. u. erg. Aufl.—Editio Cantor Aulendorf, 1981 ISBN 3 87193 054 7 NE: Fiedler, Herbert P.

Vestn. Oftal 'Mol., Nr. 2, 1976, Moscow (SU) Seiten 29–31, XP002034466 Kondrat'Eva, T.S.; et al "Study of the Hypotensive and Myotic Effects Of Various Pilocarpine Solutions (experimental studies)" siehe das ganze Dokument.

Farmatsiya, Bd. 19, Nr. 1,1970, Moscow (SU), Seiten 23–26, XP002034467 Ivanova, L. A.; et al.: "Enhanced Antimicrobial Stability of Ointment Bases" Siehe das ganze Dokument.

Ann. Acad, Med. Silesiensis Nr. 23, 1991, Katowice (PL), Wojdak, Halina; et al.: "Assessment of the Effect of Excipients Upon the Stability of Sefril and Indomethacin in Eye Preparations" Siehe das ganze Dokument.

Ann. Acad. Med Siles, 1991, 23, S 91–99 Halina Wojdak, Bozena Drobnicka, Nina Janas, Malgorzata Gadomska–Nowak Bewertungdes Einflusses von Hilfsmittelnauf die Stabilitat von Cefradyn und Indometacin in Augenarzneien.

Europaisches Arzneibuch 3.Ausgabe 1997 Deutscher Apotheker Verlag Stuttgart Govi–Verlag Pharmazeutischer Verlag GmbH Eschborn.

Dolder—Skinner Ophthalmika Pharmakologie, Biopharmazie und Galenik der Augenarzneimittel 4. Auflage.

118:27261 CA "Assessment of the Effect of Excipients Upon the Stability of Sefril and Indomethacin in Eye Preparations" Wojdak, Halina; Drobnicka, Bozena; Janas, Nina; Gadomska–Nowak, Molgorzata Zakl. Farm. Aptecznej, Slask, Akad. Med., Katowice, Pol. Ann. Acad, Med, Silesiensis (1991), 23, 91–100 CODEN: ANSID6; ISSN: 0208–5607 Journal Polish 63–5 Pharmaceuticals.

73:7184 CA "Enhanced Antimicrobial Stability of Ointment Bases" Ivanova, L.A.; Kondrat'eva, T. S. Mosk. Med, Inst. im. Sechenova, Moscow, USSR Farmatsiya (Moscow) (1970), 19(1), 23–6 CODEN:FRMTAL Journal Russian 63 Pharmaceuticals.

85:149065 CA Study of the Hypotensive and Myotic Effects of Various Pilocarpine Solutions (experimental studies) Kondrat'eva, T. S.; Denisova, T. V.; Bunin, A. Ya.; Yakovlev, A. A. Mosk. Med, Inst. im. Sechenova, Moscow, USSR Vestn, Oftal'mol. (1976), (2), 29–31 CODEN:VEOFA6 Journal Russian 63–6 Pharmaceuticals.

* cited by examiner

*Primary Examiner*—Zohreh Fay
(74) *Attorney, Agent, or Firm*—John E. Thomas

(57) ABSTRACT

Ophthalmic composition with prolonged residence time on the eye, in particular in the form of a gel which can be administered as drops, of an ointment or the like, containing a free-flowing vehicle with increased viscosity and a preservative, and, where appropriate, one or more active ingredients and conventional additives such as tonicity agents, substances to adjust the pH etc. The preservative is essentially formed according to the invention by a benzyllauryldimethylammonium salt. The invention furthermore relates to the use of a benzyllauryldimethylammonium salt as preservative for producing ophthalmic compositions intended for repeated use over lengthy periods and/or formulated for a lengthy residence time on the eye after each use, whereby irritation and/or damage to the tissue of the eye are avoided.

2 Claims, No Drawings

OPHTALMIC COMPOUND WITH EXTENDED DWELL TIME ON THE EYE

This application is a 371 of PCT/EP97/01138 filed on Jun. 3, 1997.

The invention relates to an ophthalmic composition with prolonged residence time on the eye, in particular in the form of a gel which can be administered as drops, of an ointment or the like, containing a free-flowing vehicle with increased viscosity and a preservative, and, where appropriate, one or more active ingredients and conventional additives such as tonicity agents, substances to adjust the pH etc. The invention additionally relates to the use of a benzyllauryldimethylammonium salt for producing ophthalmic compositions.

Ophthalmic compositions may, like other pharmaceutical products too, be contaminated by microorganisms of a wide variety of species. The possibility of such microorganisms entering the eye and getting onto the mucosa of the eye on use of the ophthalmic composition must be avoided. Ophthalmic products must therefore comply with strict sterility requirements. This is why products of this type are always produced under sterile conditions.

In order to increase the sterility and, in particular, the shelf life of ophthalmic products which are not intended for immediate use, preservatives are added to them. On the one hand, the latter must have a sufficiently microbicidal effect to ensure the permanent sterility of the product, and on the other hand they must not themselves lead to irritation or tissue damage in the eye, which is, after all, often already damaged.

These requirements are particularly crucial in the case of ophthalmic compositions which must be used repeatedly over lengthy periods (one or more days or longer) so that a permanent level of preservatives is set up in the eye. In this case the risk of irritation or even tissue damage by the preservative is particularly great.

This is similarly true of those ophthalmic compositions, which show prolonged (by comparison with products which can easily be washed out by tear fluid, such, as for example, conventional aqueous dropper solutions) residence time on or in the eye after a single use. Products of this type are, with regard to their consistency, adjusted to have an increased viscosity. One example are aqueous products which are gelatinously thickened by adding water-soluble polymers, is particular gels which can be administered as drops. Another example are the well-known ointments, usually in the form of spreadable emulsions.

Preservatives used for such purposes are, for example, thiomersal, cetrimide and similar substances.

Another preservative which is frequently suggested for ophthalmic products is benzalkonium chloride.

Benzalkonium chloride is the international nonproprietory name for N-alkyl-N-benzyl-N,N-dimethyl-ammonium chloride with alkyl radicals between $C_8H_{17}$ and $C_{18}H_{37}$. Benzalkonium chloride is normally obtained from natural fats or oils and is a mixture of varying composition, depending on the raw materials used, of the quaternary compounds described above.

Unless other indicated, the term "benzalkonium" in this application always means such a mixture with different alkyl radicals, with the number of carbon atoms in the alkyl radical varying from $C_8$ to $C_{18}$.

U.S. Pat. No. 4,053,628 discloses a clear solution of sodium cromoglicate to which a large number of preservatives can be added. Suggested and exemplified besides thiomersal, cetrimide, benzethonium chloride and others is also benzalkonium chloride. The possibility of adjusting the viscosity of such solutions is mentioned in general; however, the examples relate exclusively to solutions without viscosity-modifying additives. The risk of eye irritation due to the preservative is not mentioned in this publication.

U.S. Pat. No. 4,271,143 has disclosed the use of benzalkonium chloride as preservative in an ophthalmic gel for delayed release of active ingredient. There is no report of eye irritation with the envisaged long residence time in the eye. The tests on the eye described in U.S. Pat. No. 4,171,143 each lasted only a few hours. This is possibly the reason why the problems which occur with such gels on prolonged use apparently were not observed.

Benzalkonium chloride has excellent antiseptic properties even in ophthalmic preparations, especially in aqueous ophthalmic preparations. However, benzalkonium chloride is, as has emerged since publication of the abovementioned patents, poorly tolerated and may lead to irritation and even damage of the eye. B. Lopez et al. (Current Eye Research, 1991, 10 (7) 645 to 656) report on the injurious effect of preservatives in simulated tear fluids on the cornea of rabbits. The effect of tear fluids preserved with 0.01% benzalkonium chloride, 0.001% polyquat or 0.004% thiomersal was related to that in a comparison group in which the simulated tear fluid was used without preservative.

The measure chosen for the damage to the cornea was the increase in the ability to take up carboxyfluorescein. Simulated tears which contained polyquat or thiomersal brought about an increase in uptake of one to four-fold. Simulated tears which contained benzalkonium chloride brought about an increase in uptake of about 10 to 100-fold.

Checks by examination under the electron microscope demonstrated that the increase in the ability to take up carboxyfluorescein was associated with increased cell damage in the cornea. As a result, urgent advice against the use of benzalkonium salts in ophthalmic products was given.

Individual benzalkonium components have attracted interest recently. Thus, JP-A 1246227 describes a method for avoiding incompatibilities in liquid aqueous ophthalmic compositions, especially eye drops, which contain benzalkonium chloride. A large number of medicinal active ingredients shows incompatibility with benzalkonium chloride in the dosage form as aqueous solution, leading to the formation and flocculation of soluble compounds. It is therefore impossible to use benzalkonium chloride as preservative in such aqueous compositions. When virtually pure benzyllauryldimethylammonium chloride, that is to say the $C_{12}$ homologue from the benzalkonium chloride mixture, is used, the described incompatibilities do not occur. It is thus possible to preserve eye drops whose active ingredient is incompatible with benzalkonium chloride by using benzyllauryldimethylammonium chloride.

This prior art has no relation to the problem of the lack of tolerability of benzalkonium chloride in the eye.

It is an object of the present invention to provide an ophthalmic composition of the type mentioned at the outset which is well tolerated by the eye, even on persistent exposure, and which overcomes the disadvantages of the prior art without, at the same time, losing the advantageous effects of the benzalkonium salts as preservatives.

Achievement of this object is made possible according to the invention by the features of the independent claims.

The independent claims define advantageous embodiments of the invention.

It has been found, surprisingly, that on use of benzyllauryldimethylammonium salts as preservatives in ophthalmic products there is distinctly less or even no irritation and damage in the eye, which are observed, however, on use of other preservatives, including benzalkonium chloride.

The invention therefore makes it possible in particular to preserve those ophthalmic compositions intended to have a prolonged residence time on the eye by comparison with eye drops or the like. It is possible, in particular in this way to produce gels which can be administered as drops, ointments and the like to which the eye is exposed for a very long time after a single use, because they are only slowly washed out by the tear fluid, the preservative having all the advantages of the known benzalkonium chloride but without eye-irritant or even eye-damaging effect.

The ophthalmic compositions according to the invention are preferably those which have as vehicle an aqueous basis for a gel which can be administered as drops. In this case, a viscosity-increasing synthetic or natural polymer in aqueous solution or aqueous dispersion will be employed in a known manner.

Particularly suitable for this purpose are the carboxyvinyl polymers already known as gel formers, especially carboxypolymethylenes which are commercially available under the trade name "Carbopol". It is alternatively possible to employ the ethylene/maleic anhydride copolymers which are commercially available under the trade name "EMA".

Particularly suitable natural polymers are the various cellulose derivatives which are in turn already known for ophthalmic gels, especially alkylcelluloses, hydroxycelluloses, hydroxyalkylcelluloses etc. It is possible with advantage to use in addition or as alternative natural gums such as, for example, guar gum, xanthan gum etc. Other example of natural polymers which can be used advantageously according to the invention are dextran and its derivatives.

It may be advantageous to formulate the ophthalmic composition according to the invention as in principle a single-phase aqueous liquid in which the other ingredients occur in solution or as dispersed particles.

It is an alternative and often even more advantageous possibility to build up the composition as a two-phase liquid with an aqueous and a hydrophobic phase. Especially if the product contains particular active ingredients such as, for example, vitamin A, it will be preferred to provide a continuous, aqueous phase with droplets of the hydrophobic phase emulsified therein. Suitable as hydrophobic phase are oils, medium chain-length triglyerides etc. Medium chain-length triglycerides will advantageously be used as hydrophobic phase particularly in products which contain vitamin A as active ingredient.

The concentration of the benzyllauryldimethylammonium salt corresponds to the usual concentrations employed for benzalkonium chloride. The benzyllauryldimethylammonium salt is preferably simply the chloride.

Besides the ophthalmic compositions which have just been described and have been formulated for prolonged residence time on the eye after each use, the advantage of the invention can also be utilized for those ophthalmic compositions which, although they contain no viscosity-increasing ingredients, (which thus delay washing out), must be used repeatedly over lengthy periods and thus likewise result in a continuously elevated level of preservative in the eye. Products of this type may also lead to irritation or even tissue damage if harmful preservatives are present, and therefore the advantage of the invention may also be used for such products by employing the benzyllauryldimethylammonium salt as preservative in place of these preservatives.

Examples thereof are not only eye drops but also simulated tear fluid as in the test reported by Lopez et al.

The following examples serve merely to illustrate the invention and represent no restriction whatsoever.

EXAMPLE 1

Ophthalmic compositions with 0.01% benzyllauryldimethylammonium chloride.

Batch size: 2 kg

| Ingredients | Amount in grams |
| --- | --- |
| Carbopol 980 NF | 4.00 |
| Benzyllauryldimethylammonium chloride | 0.2000 |
| Sorbitol | 80.00 |
| NaOH, solid | 1.57 |
| Water | (remainder up to batch size) |

EXAMPLE 2

Ophthalmic composition with 0.005% benzyllauryldimethylammonium chloride.

Batch size: 2 kg

| Ingredient | Amount in grams |
| --- | --- |
| Carbopol 980 NF | 4.00 |
| Benzyllauryldimethylammonium chloride | 0.1000 |
| Sorbitol | 80.00 |
| NaOH, solid | 1.57 |
| Water | (remainder up to batch size) |

Long-term tests were carried out on experimental rabbits (Charles River) with the compositions of Example 1 and 2. In parallel, comparative tests were carried out with a corresponding control group in which the compositions employed were in every respect the same but differed with regard to the preservative. Instead of benzyllauryldimethylammonium chloride, on the one hand benzalkonium chloride was used in the same concentration, and on the other hand, thiomersal (standard concentration) =40 $\mu$g/g was used.

The test lasted 5 weeks.

At the end of the test, seven of eight rabbits in the control group treated with the composition with thiomersal as preservative showed severe irritation, and in some cases also damage to the eye.

In the control group which received a product with benzalkonium chloride as preservative, all the rabbits show sever irritation, and some showed damage to the tissue of the eye, at the end of the investigation.

By contrast, the ophthalmic compositions of Examples 1 and 2 according to the invention led to no detectable irritation in the eye of any rabbit at the end of the test period. Likewise, no tissue damage whatsoever was observed.

What is claimed is:

1. A method of minimizing eye irritation of a preserved ophthalmic composition, comprising employing benzyllauryldimethylammonium salt in an amount effective to preserve the composition, wherein irritation or damage to eye tissue is avoided even when the composition is applied to eye tissue repeatedly over a lengthy period or resides on eye tissue for a lengthy period.

2. The method of claim 1, comprising employing benzyllauryldimethylammonium chloride in an amount effective to preserve the composition.

* * * * *